US00PP28636P2

(12) United States Plant Patent
Hansen

(10) Patent No.: US PP28,636 P2
(45) Date of Patent: Nov. 14, 2017

(54) ***DIANTHUS* PLANT NAMED 'PAINT THE TOWN FUCHSIA'**

(50) Latin Name: ***Dianthus* hybrid**
Varietal Denomination: Paint The Town Fuchsia

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/330,908

(22) Filed: Nov. 14, 2016

(51) Int. Cl.
*A01H 5/02* (2006.01)

(52) U.S. Cl.
USPC ..... Plt./277

(58) Field of Classification Search
USPC ..... Plt./277
CPC ..... A01H 5/0233
See application file for complete search history.

*Primary Examiner* — Kent L Bell

(57) ABSTRACT

A new and unique cultivar of perennial carnation or pinks, *Dianthus* plant named 'Paint the Town Fuchsia' with numerous, single, fragrant flowers of fringed fuchsia petals in a strong flush in late spring, continuing until mid-fall, over finely-textured blue-green foliage. *Dianthus* 'Paint the Town Fuchsia' has vigorous compact habit, is tolerant of high temperatures, resists center die-out and does not require vernalization for effective flowering.

1 Drawing Sheet

Botanical denomination: *Dianthus* hybrid.
Cultivar designation: 'Paint the Town Fuchsia'.

BACKGROUND OF THE INVENTION

The present invention relates to the new and distinct cultivar of carnation or pinks from the genus *Dianthus* and given the cultivar name 'Paint the Town Fuchsia'. The new plant was the result of an intentional cross on Jun. 12, 2012 by the inventor at a wholesale perennial nursery in Zeeland, Mich., USA between *Dianthus* 'Neon Star' U.S. Plant Pat. No. 14,549 times and 'Kahori' (not patented). Seeds of the cross were harvested Jul. 2, 2012. The new hybrid was first isolated from trials at a wholesale perennial nursery in Zeeland, Mich. during the summer of 2013 as a single seedling and given the breeder number 12-94-4 during the remaining evaluation processes. *Dianthus* 'Paint the Town Fuchsia' has been asexually propagated at the same nursery in Zeeland, Mich. since 2012 using traditional shoot tip cutting procedures and found to reproduce plants that are identical and exhibit all the characteristics of the original plant.

No plants of *Dianthus* 'Paint the Town Fuchsia' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Comparing the new plant with the female parent, 'Neon Star', the new plant has a slightly taller habit in flower, is also broader in width, has a longer flowering season, and the flower colors are slightly different. Compared to the male parent, 'Kahori', the new plant is wider in habit, has foliage with more blue coloration, and the flower color is slightly different. Other similar *Dianthus* include: 'Witch Doctor' (not patented) and 'Love Doctor' (not patented). *Dianthus* 'Paint the Town Fuchsia' has foliage that is more blue than either of these two. It is most similar in habit to 'Witch Doctor', but is more compact than 'Love Doctor'. The flower color of 'Witch Doctor' is more raspberry and the flower color of 'Love Doctor' is a softer pink and not as intense fuchsia as the new plant.

*Dianthus* 'Paint the Town Fuchsia' is distinct from its parents and all other *Dianthus* known to the applicant in the following combined traits:

1. Single flowers with five overlapping petals of fuchsia.
2. Petals having a deeply serrated apex.
3. Numerous flowers per peduncle with many flowers on heavily branched stems.
4. Prolonged flowering period with a strong flush in late spring and continuing to mid-fall.
5. Small flower size producing a sweetly spicy fragrance.
6. High heat tolerance with no vernalization required for flower production.
7. Floriferous, vigorous, with compact habit and finely-textured blue-green foliage.

BRIEF DESCRIPTION OF THE DRAWINGS

The photographs of the *Dianthus* 'Paint the Town Fuchsia' demonstrate the overall appearance, including the unique traits, of a two-year-old plant in a full-sun trial garden. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
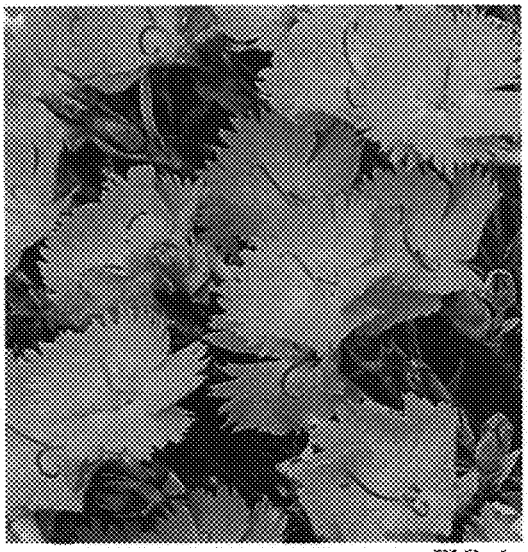
FIG. 1 shows a close-up of the flowers and buds.
Figure 2:
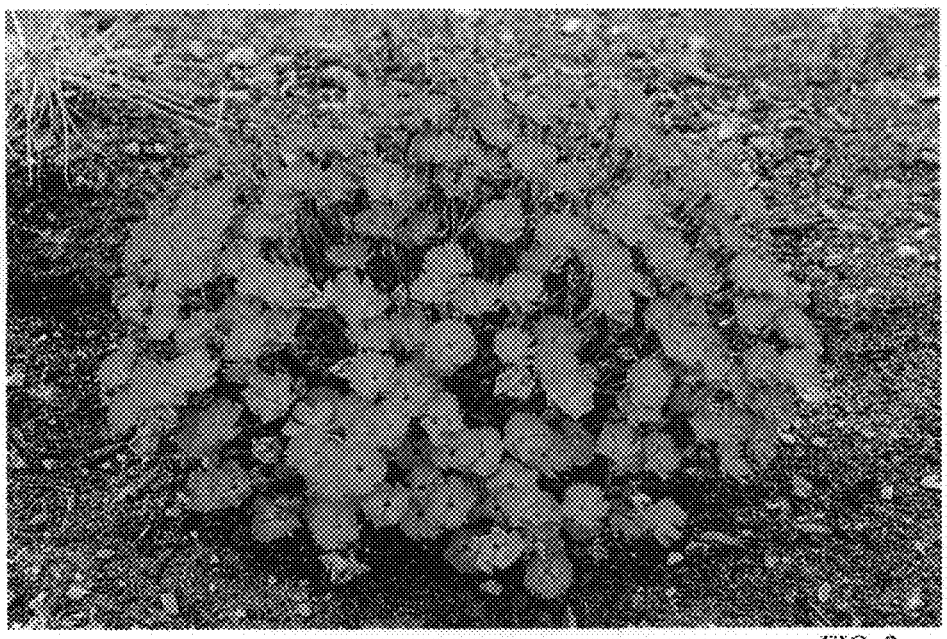
FIG. 2 shows the habit of the plant in early-season flowering.

The following detailed description of the new plant is based on observations of two-year-old plants in full-sun trial garden at a wholesale perennial nursery in Zeeland, Mich., USA with supplemental watering, light additions of fertilizer and free of pinching or plant growth regulators. All color usage is in accordance with the 2001 edition of The Royal Horticultural Colour Chart except where common dictionary terms are used.

Botanical classification: *Dianthus* hybrid.

Parentage: 'Neon Star' U.S. Plant Pat. No. 14,549 as the female or seed parent and 'Kahori' (not patented) as the male or pollen parent.

Plant description:

*Habit*.—Caespitose, herbaceous, evergreen perennial; erect stems and finely-branched peduncles, large number of flowers; height of foliage about 12.0 cm and about 44.0 cm across; height in flower is about 20.0 cm.

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous on adaxial and abaxial; margin entire to microscopically serrulate; acute apex; base decurrent, adpressed along stem and slightly perfoliate; no fragrance detected.

*Leaf dimensions*.—To about 3.9 cm long and about 5.0 mm wide, average about 3.6 cm long and 3.5 mm wide.

*Leaf color*.—Young expanding leaves abaxial and adaxial nearest RHS 137B; mature adaxial and abaxial nearest RHS 137B.

*Venation*.—Not pronounced; obscurely pinnate, coloration same as that of leaf top and bottom.

Stems: Beginning erect and becoming arching with development of flowers; terete, glabrous, glaucous, branching at alternate nodes; about 100 per plant.

*Stem size*.—About 16.0 cm long and about 2.5 mm diameter at base.

*Stem color*.—Between RHS 138A and RHS 1438B with blushing of nearest RHS 183C.

*Branching*.—Numerous; typically alternate, from upper and lower leaf axils; about 12 per main stem; branch length average about 3.5 cm at time of initial flowering.

*Nodes*.—About 11 to 12 per stem; about 4.0 mm diameter; color nearest RHS 138B with tinting of nearest RHS 187A.

*Internodes*.—Average about 0.5 cm apart depending on growing temperature, shorter in cooler conditions.

Inflorescence:

*Type*.—Terminal, cymose; salverform.

*Attitude*.—Upright.

*Dimension*.—About 6.0 cm above foliage.

*Flowers per stem*.—Typically two, rarely one or three.

*Pedicel*.—Glaucous, glabrous, terete.

*Pedicel size*.—Terminal flower about 1.3 cm long and about 1.5 mm diameter; other flowers average about 1.0 cm long and 1.0 mm diameter.

*Pedicel color*.—Nearest RHS 137A and nearest RHS N138D with glaucous bloom.

*Flower*.—Perfect; actinomophic; single; about 200 flowers per plant in peak late spring.

*Flower bud one day prior to opening*.—Glaucous, glabrous, long ellipsoid with rounded apex and rounded base.

*Flower bud size*.—One day prior to opening — about 2.2 cm long and about 4.0 mm wide; style protruding about 1.5 mm.

*Flower bud color*.—With petals exposed and still tight — petals nearest RHS N78A.

*Flower period*.—Beginning with strong flush in late spring and continuing more sparsely through mid-fall; effective about twenty-two weeks per flowering season.

*Flower fragrance*.—Light, sweet spicy, clove-like.

*Flower lasting quality*.—About six days on or cut from plant.

*Petals*.—Glabrous except at base of limb pubescent; five per flower; consisting of a rounded blade or limb and a claw; limb and claw combined are obovate with long tapered claw; apex and margin with coarse dentations 3.5 mm deep; limb bent outwardly in distal 10.0 mm to nearly a ninety degree angle; claw tapering to attenuate base about 1.0 mm across; persistent.

*Petal color*.—Young adaxial nearest RHS N78A in distal limb, proximal limb nearest RHS N78B with three faint stripes of nearest RHS N78A, claw portion nearest RHS 155D in base and claw between base and limb nearest RHS 145D; young abaxial nearest RHS N78D in distal limb, proximal limb lighter than RHSN78D, claw base nearest RHS 145D and claw portion between base and limb nearest RHS 145C; mature adaxial limb nearest RHS N78C, claw base nearest RHS 155D and claw between base and limb nearest RHS 145C; mature abaxial limb lighter than RHS N78D, claw base nearest RHS 145D and claw between base and limb nearest RHS 145C.

*Petal dimension*.—Average about 29.0 mm long and 16.0 mm across at widest part of limb; claw portion average about 12.0 mm long and about 1.0 mm at base; limb portion about 17.0 mm long and 16.0 mm wide.

*Calyx*.—Glabrous, glaucous; margins entire; consisting of five sepals with acute apex and fused base forming five-toothed corolla tube fused in proximal 8.0 mm; individually about 1.2 cm long and about 2.0 mm across at fusion; campanulate to about 12.0 mm long and about 4.0 mm in diameter.

*Calyx color*.—Abaxial between RHS 137A and RHS 137B with slight blushing of between RHS 187B and RHS 187C; adaxial nearest RHS 138C.

*Peduncle*.—Glabrous, glaucous, terete, about 4.0 cm long and about 2.0 mm diameter at base.

*Peduncle color*.—Nearest RHS 137A.

*Bracts*.—Two pair, opposite, glaucous, glabrous; sessile; margin entire, broadly obtuse to deltoid with acute apex; outer pair about 6.0 mm long and about 3.0 mm wide; inner pair about 6.0 mm long and about 4.0 mm wide.

*Bract color*.—Abaxial and adaxial nearest RHS 139B with adaxial and abaxial 1.0 mm wide blushed margins nearest RHS 187B.

*Androecium*.—Typically ten, rudimentary; fused in basal phalange. Filaments: phalange about 2.0 mm long, total about 6.0 mm long; average total about 4.5 mm long and 0.3 mm diameter; color phalange nearest RHS 145A and separate filament nearest RHS 155D. Anther: typically rudimentary; flattened ellipsoid; dorsifixed; about 1.0 mm long and about 0.5 mm across; color nearest RHS158A. Pollen: not observed.

*Gynoecium*.—Style: typically split in two just above ovary. Pistil: glabrous abaxial surface and puberulent adaxial surface; curled in distal 4.0 mm; about 14.0 mm long and about 1.0 mm diameter; color adaxial nearest RHS N81A, abaxial whiter than RHS 155D proximally with distal tinting of between RHS N81A and RHS N79C. Stigma: puberulent; about 0.6 mm long and 0.6 mm wide; with a slight furrow running parallel to the style; slightly curled; color nearest RHS N81A. Ovary: superior; ellipsoid-shaped; about 7.0 mm long and about 3.0 mm wide; color nearest RHS 146B.

Fruit: Capsule; oblong ovoid to cylindrical with rounded base and acute apex; opening by 4 teeth; about 3.0 mm long and 2.5 mm diameter; color between RHS 164B and RHS 164C when dried.

Seed: Not observed.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

It is claimed:

1. A new and distinct *Dianthus* plant named 'Paint the Town Fuchsia' essentially as herein described and illustrated.

* * * * *